United States Patent [19]

Malherbe et al.

[11] Patent Number: 5,300,647

[45] Date of Patent: *Apr. 5, 1994

[54] O-CARBONYL N-HYDROXY HINDERED AMINE STABILIZERS

[75] Inventors: Roger F. Malherbe, Basel, Switzerland; Roland A. E. Winter, Armonk; James P. Galbo, Hartsdale, both of N.Y.

[73] Assignee: Ciba-Geigy Corporation, Ardsley, N.Y.

[ * ] Notice: The portion of the term of this patent subsequent to Apr. 20, 2010 has been disclaimed.

[21] Appl. No.: 68,566

[22] Filed: May 28, 1993

Related U.S. Application Data

[63] Continuation of Ser. No. 988,388, Dec. 8, 1992, abandoned, which is a continuation of Ser. No. 883,810, May 12, 1992, abandoned, which is a continuation of Ser. No. 749,472, Aug. 15, 1991, abandoned, which is a continuation of Ser. No. 595,713, Oct. 9, 1990, abandoned, which is a continuation of Ser. No. 259,956, Oct. 19, 1988, abandoned, and a continuation-in-part of Ser. No. 99,419, Sep. 21, 1987, abandoned.

[51] Int. Cl.⁵ ............... C07D 211/36; C07D 211/30; C07D 401/00; C07D 403/00

[52] U.S. Cl. .................... 546/188; 546/189; 546/225; 546/262; 540/524; 540/525; 544/194; 544/207; 544/231; 544/357; 544/360

[58] Field of Search ............. 546/188, 189, 225, 242, 546/525, 524; 544/194, 207, 231, 357, 360

[56] References Cited

U.S. PATENT DOCUMENTS

| | | | |
|---|---|---|---|
| 4,465,757 | 8/1984 | Leppard et al. | 430/216 |
| 4,691,015 | 10/1987 | Behrens | 544/198 |
| 5,204,473 | 4/1993 | Winter et al. | 546/188 |

FOREIGN PATENT DOCUMENTS 0104146  3/1984  European Pat. Off.

OTHER PUBLICATIONS

Kurumada J Polymer Sci 22:277-81, 1984.

Primary Examiner—John W. Rollins
Attorney, Agent, or Firm—Luther A. R. Hall

[57] ABSTRACT

Hindered amines based on various 2,2,6,6-tetraalkylated nitrogen-containing heterocyclic moieties wherein the hindered nitrogen atom on the ring is substituted with O-acyl, O-carbamoyl or O-carbonate substituents and the 4-position of the ring is substituted with a variety of groups, are effective as light stabilizers in diverse substrate systems.

9 Claims, No Drawings

O-CARBONYL N-HYDROXY HINDERED AMINE STABILIZERS

This is a continuation of application Ser. No. 07/988,388, filed on Dec. 8, 1992, now abandoned, which is a continuation of application Ser. No. 07/883,810, filed on May 12, 1992, now abandoned, which is a continuation of application Ser. No. 07/749,472, filed on Aug. 15, 1991, now abandoned, which is a continuation of Ser. No. 07/595,713, filed Oct. 9, 1990, now abandoned, which is a continuation of Ser. No. 07/259,956, filed on Oct. 19, 1988, now abandoned, which is a continuation-in-part of application Ser. No. 07/099,419, filed on Sep. 21, 1987, now abandoned.

BACKGROUND OF THE INVENTION

The invention relates to novel hindered amine derivatives containing 0-acyl, 0-carbamoyl or 0-carbonate groups on the hindered nitrogen atom of the nitrogen-containing heterocyclic ring and a diversity of substituents on the 4-position of the ring.

Various N-acyloxy and N-carbamoyloxy hindered amine derivatives have been disclosed. N-Acetoxy and N-benzoyloxy derivatives prepared from the N-hydroxy starting material are described in Kurumada et al, *J. Polym. Sci.* Polym. Chem. Ed. 22, 277-81 (1984). Felder et al., *Helv. Chim. Acta.* 63, 132 (1980) teach the preparation of an N-phenylacetoxy derivative. N-(Phenylcarbamoyl)oxy derivatives of N-hydroxy hindered amines have been reported in Rozantsev et al, *Isv. Akad. Nauk SSSR.* Ser. Khim. 5, 891-6 (1966). The bis(N-acetoxypiperidyl) sebacate has been disclosed in Carlsson et al, *Polym. Science Technol.* 26, 35-47 (1984). Finally, U.S. Pat. No. 4,472,547 discloses various N-piperidyl lactam compounds such as an N-benzoyloxy hindered amine containing a 4-(2-oxohexamethyleneimine) substituent as light stabilizers for polyolefins and other organic polymers.

The instant invention relates to hydroxylamine derivatives having one of formulae A to P

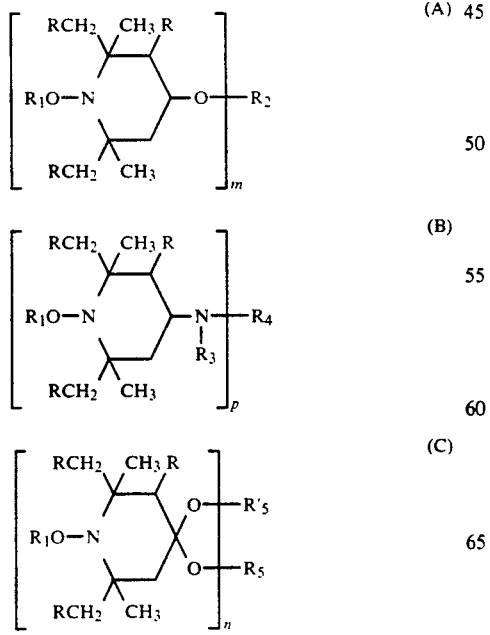

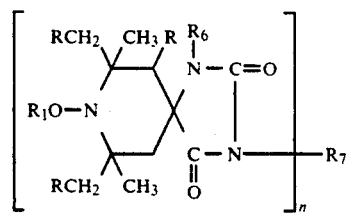

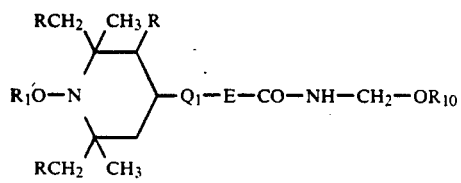

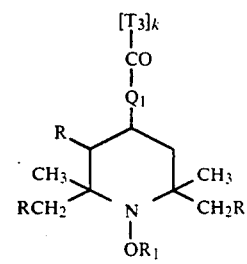

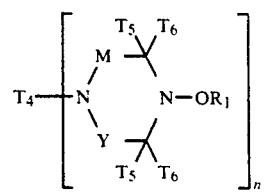

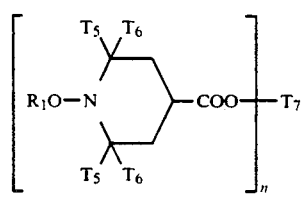

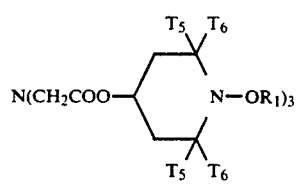

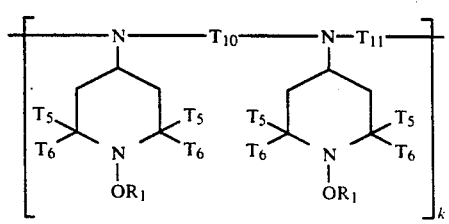

-continued

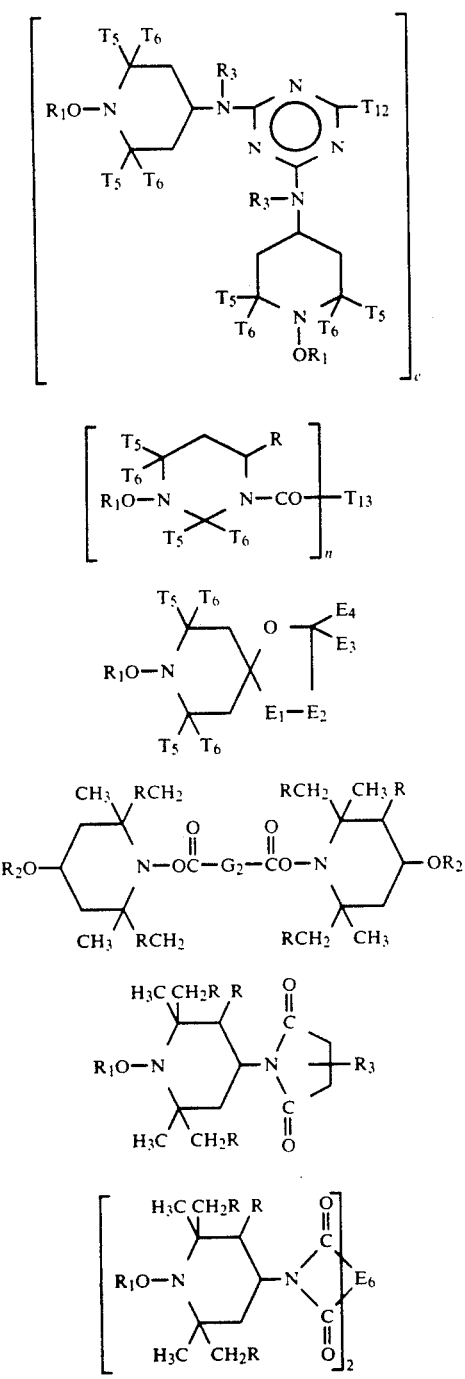

wherein
R is hydrogen or methyl,
R₁ is

wherein D is $C_1-C_{18}$ alkyl, $C_1-C_{18}$ alkoxy, phenyl, phenyl substituted by hydroxy, alkyl or alkoxy, or amino or amino mono- or disubstituted by alkyl or phenyl;
m is 1-4,
when m is 1,
R₂ is (K)

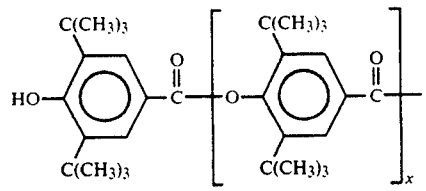

wherein x is 0 or 1, or (L)

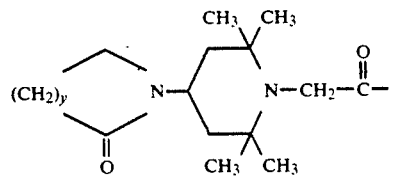

wherein y is 2-4;
when m is 2 and D is alkyl, phenyl or substituted phenyl, (M) R₂ is $C_1-C_{12}$ alkylene, $C_4-C_{12}$ alkenylene, xylylene, a divalent acyl radical of a cycloaliphatic, araliphatic or aromatic dicarboxylic acid or of a dicarbamic acid, preferably an acyl radical of a cycloaliphatic or aromatic dicarboxylic acid having 8-14 C atoms, or of an aliphatic, cycloaliphatic or aromatic dicarbamic acid having 8-14 atoms;

(N)

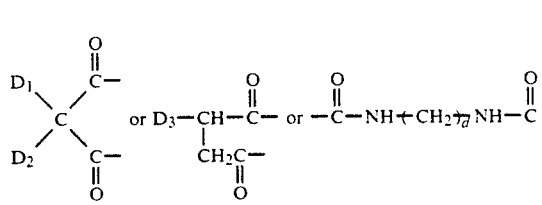

(O)

wherein D₁ is an aryl or aralkyl radical including 3,5-di-t-butyl-4-hydroxybenzyl radical, D₂ is D₁ or hydrogen, D₃ is an alkenyl radical containing up to 18 carbon atoms, and d is 0-20;
when m is 2 and D is amino, substituted amino or alkoxy, (P) R₂ is $C_1-C_{12}$ alkylene, $C_4-C_{12}$ alkenylene, xylylene, a divalent acyl radical of an aliphatic, cycloaliphatic, araliphatic or aromatic dicarboxylic acid, or of a dicarbamic acid; preferably an acyl radical of an aliphatic dicarboxylic acid having 2-18 C atoms, of a cycloaliphatic or aromatic dicarboxylic acid having 8-14 C. atoms, or of an aliphatic, cycloaliphatic or aromatic dicarbamic acid having 8-14 C atoms;

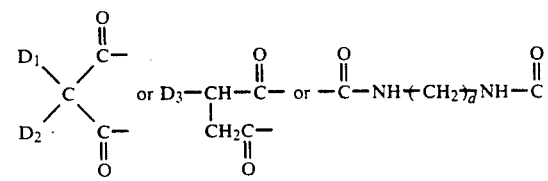

wherein D₄ and D₅ are independently hydrogen, an alkyl radical containing up to 8 carbon atoms, an aryl or aralkyl radical including 3,5-di-t-butyl-4-hydroxybenzyl radical, D₆ is hydrogen, or an alkyl or alkenyl radical containing up to 18 carbon atoms, and d is 0–20;

when m is 3, $R_2$ is a trivalent acyl radical of an aliphatic, unsaturated aliphatic, cycloaliphatic, or aromatic tricarboxylic acid;

when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;

p is 1, 2 or 3, $R_3$ is hydrogen, $C_1$–$C_{12}$ alkyl, $C_5$–$C_7$ cycloalkyl, $C_7$–$C_9$ aralkyl, $C_2$–$C_{18}$ alkanoyl, $C_3$–$C_5$ alkenoyl or benzoyl;

when p is 1, $R_4$ is hydrogen, $C_1$–$C_{18}$ alkyl, $C_5$–$C_7$ cycloalkyl, $C_2$–$C_8$ alkenyl unsubstituted or substituted by a cyano, carbonyl or carbamide group, aryl, aralkyl, or it is glycidyl, a group of the formula —CH₂—CH(OH)—Z or of the formula —CO—Z— or —CONH—Z wherein Z is hydrogen, methyl or phenyl; or a group of the formulae

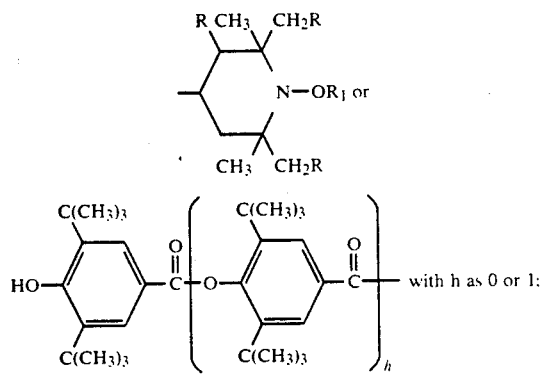

when p is 2, $R_4$ is $C_1$–$C_{12}$ alkylene, $C_6$–$C_{12}$ arylene, xylylene, a —CH₂CH(OH)—CH₂ group, or a group —CH₂—CH(OH)—CH₂—O—X—O—CH₂—CH(OH)—CH₂— wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—; or $R_3$ and $R_4$ together when p is 1 can be alkylene of 4 to 6 carbon atoms or 2-oxo polyalkylene or the cyclic acyl radical of an aliphatic or aromatic 1,2- or 1,3-dicarboxylic acid, or

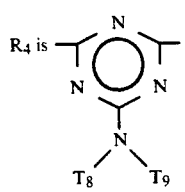

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, preferably $T_8$ and $T_9$ together are 3-oxapentamethylene;

when p is 3, $R_4$ is 2,4,6-triazinyl.

when n is 1, $R_5$ and $R'_5$ are independently $C_1$–$C_{12}$ alkyl, $C_2$–$C_{12}$ alkenyl, $C_7$–$C_{12}$ aralkyl, or $R_5$ is also hydrogen, or $R_5$ and $R'_5$ together are $C_2$–$C_8$ alkylene or hydroxyalkylene or $C_4$–$C_{22}$ acyloxyalkylene;

when n is 2, $R_5$ and $R'_5$ together are (—CH₂)₂C(CH₂—)₂;

$R_6$ is hydrogen, $C_1$–$C_{12}$ alkyl, allyl, benzyl, glycidyl or $C_2$–$C_6$ alkoxyalkyl;

when n is 1, $R_7$ is hydrogen, $C_1$–$C_{12}$ alkyl, $C_3$–$C_5$ alkenyl, $C_7$–$C_9$ aralkyl, $C_5$–$C_7$ cycloalkyl, $C_2$–$C_4$ hydroxyalkyl, $C_2$–$C_6$ alkoxyalkyl, $C_6$–$C_{10}$ aryl, glycidyl, a group of the formula —(CH₂)$_m$—COO—Q or of the formula —(CH₂)$_m$—O—CO—Q wherein m is 1 or 2, and Q is $C_1$–$C_4$ alkyl or phenyl; or when n is 2, $R_7$ is $C_2$–$C_{12}$ alkylene, $C_6$–$C_{12}$ arylene, a group —CH₂CH(OH)—CH₂—O—X—O—CH₂—CH(OH)—CH₂— wherein X is $C_2$–$C_{10}$ alkylene, $C_6$–$C_{15}$ arylene or $C_6$–$C_{12}$ cycloalkylene, or a group —CH₂CH(OZ')CH₂—(OCH₂—CH(OZ')CH₂)₂— wherein Z' is hydrogen, $C_1$–$C_{18}$ alkyl, allyl, benzyl, $C_2$–$C_{12}$ alkanoyl or benzoyl;

$Q_2$ is —N($R_8$)— or —O—; E is $C_1$–$C_3$ alkylene, the group —CH₂—CH($R_9$)—O— wherein $R_9$ is hydrogen, methyl or phenyl, the group —(CH₂)₃—NH— or a direct bond;

$R_{10}$ is hydrogen or $C_1$–$C_{18}$ alkyl, $R_8$ is hydrogen, $C_1$–$C_{18}$ alkyl, $C_5$–$C_7$ cycloalkyl, $C_7$–$C_{12}$ aralkyl, cyanoethyl, $C_6$–$C_{10}$ aryl, the group —CH₂—CH($R_9$)—OH wherein $R_9$ has the meaning defined above; a group of the formula

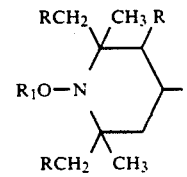

or a group of the formula

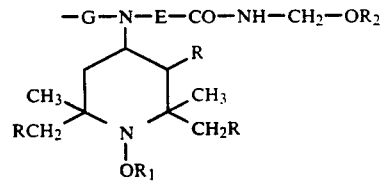

wherein G can be $C_2$–$C_6$ alkylene or $C_6$–$C_{12}$ arylene; or $R_8$ is a group —E—CO—NH—CH₂—OR₁₀;

Formula F denotes a recurring structural unit of a polymer where $T_3$ is ethylene or 1,2-propylene, or is the repeating structural unit derived from an alpha-olefin copolymer with an alkyl acrylate or methacrylate; preferably a copolymer of ethylene and ethyl acrylate, and where k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene or mixture of said hydroxylamine derivatives, preferably $T_5$ and $T_6$ are each methyl, M and Y are independently methylene or carbonyl preferably M is methylene and Y is carbonyl, and $T_4$ is ethylene where n is 2;

$T_7$ is the same as $R_7$, and $T_7$ is preferably octamethylene when n is 2, $T_{10}$ and $T_{11}$ are independently alkylene of 2 to 12 carbon atoms, or $T_{11}$ is

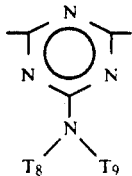

$T_{12}$ is

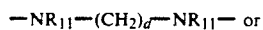

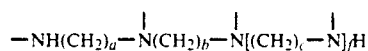

where $R_{11}$ is the same as $R_3$ or is also

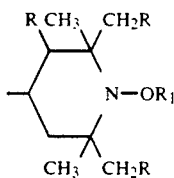

a, b and c are independently 2 or 3, and f is 0 or 1, preferably a and c are each 3, b is 2 and f is 1; and e is 3 or 4, preferably 4;

$T_{13}$ is the same as R4 with the proviso that $T_{13}$ cannot be hydrogen when p is 1;

$E_1$ and $E_{2m}$ being different, each are —CO— or —N($E_5$)— where $E_5$ is hydrogen, $C_1$-$C_{12}$ alkyl or $C_4$-$C_{22}$ alkoxycarbonylalkyl, preferably $E_1$ is —CO— and $E_2$ is —N($E_5$)—, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl, and $R_2$ of formula (N) is as previously defined when m is 1, and $G_2$ is a direct bond, $C_1$-$C_{12}$ alkylene, phenylene or —NH—G'—NH wherein G' is $C_1$-$C_{12}$ alkylene.

In the structures A to N, if any substituents are $C_1$-$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl and cyclohexyl, while typical aralkyl groups include benzyl, alpha-methyl-benzyl, alpha,alpha-dimethylbenzyl or phenethyl.

If $R_2$ is a divalent acyl radical of a dicarboxylic acid, it is for example an acyl radical of adipic acid, succinic acid, suberic acid, sebacic acid, phthalic acid, dibutylmalonic acid, dibenzylmalonic acid or (3,5-di-tert-butyl-4-hydroxybenzyl)-malonic acid, or bicycloheptenedicarboxylic acid.

If $R_2$ is a divalent acyl radical of a dicarbamic acid, it is for example an acyl radical of hexamethylenedicarbamic acid or of 2,4-toluylenedicarbamic acid.

The following compounds are examples of polyalkylpiperidine starting materials useful in making the hydroxylamine derivatives of formula A. (Depending on the selected preparative procedure).

di-(2,2,6,6-tetramethylpiperidin-4-yl)phthalate alpha,alpha'-(di-2,2,6,6-tetramethylpiperidine-4-oxy)-p-xylene 1,4-dihydroxy-2,2,6,6-tetramethylpiperidine 1-acetoxy-4-hydroxy-2,2,6,6-tetramethylpiperidine di-(1-oxyl-2,2,6,6-tetramethylpiperdin-4-yl) phthalate 1-oxyl-2,2,6,6-tetramethylpiperidin-4-one (1-hydroxy-2,2,6,6-tetramehylpiperdin-4-yl) stearate (2,2,6,6-tetramethylpiperidin-4-yl)-[4-(2-oxoazepin-1-yl)-2,2,6,6-tetramethylpiperidin-4-yl]acetate As $C_2$-$C_{18}$ alkanoyl, $R_3$ is for example propionyl, butyryl, octanoyl, dodecanoyl, hexadecanoyl, octadecanoyl, but preferably acetyl; and as $C_3$-$C_5$ alkenoyl, $R_3$ is in particular acryloyl.

If $R_4$ is $C_2$-$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$-$C_{12}$ alkylene, they are for example ethylene, propylene, 2,2-dimethylpropylene, tetramethylene, hexamethylene, octamethylene, decamethylene or dodecamethylene.

If any substituents are $C_6$-$C_{15}$ arylene, they are for example o-, m- or p-phenylene, 1,4-naphthylene or 4,4'-diphenylene.

As $C_6$-$C_{12}$ cycloalkylene, X is especially cyclohexylene.

The following compounds are examples of polyalkylpiperidine starting materials useful in making the hydroxylamine derivatives of formula B.

N,N'-bis(2,2,6,6-tetramethylpiperidin-4-yl)-hexamethylene-1,6-diamine,

N,N'-bis-(2,2,6,6-tetramethylpiperidin-4-yl)-hexamethylene-1,6-diacetamide, 4-benzylamino-2,2,6,6-tetramethylpiperidine, N-n-butyl-N-(2,2,6,6-tetramethylpiperidin-4-yl)-4-hydroxy-3,5-di-tert.butylbenzamide, N,N'-bis-(2,2,6,6-tetramethylpiperidin-4-yl)-N,N'-dibutyl-adipamide, N,N'-bis-(2,2,6,6-tetramethylpiperidin-4-yl)-N,N'-dicyclohexyl-(2-hydroxypropylene-diamine), N,N'-bis-(2,2,6,6-tetramethylpiperidin-4-yl)-p-xylylenediamine, 4-(3-methyl-4-hydroxy-5-tert-butyl-benzoyl acetamido)-2,2,6,6-tetramethylpiperidine, alpha-cyano-β-methyl-β-[N-(2,2,6,6-tetramethylpiperidin-4-yl]-amino-acrylic acid methyl ester, 1-acetoxy-4-butylamino-2,2,6,6-tetramethyl piperidine 1-oxyl-2,2,6,6-tetramethylpiperidin-4-one.

If R5 is $C_2$-$C_8$ alkylene or hydroxyalkylene, it is for example ethylene, 1-methyl-ethylene, propylene, 2-ethylpropylene or 2-ethyl-2-hydroxymethylpropylene.

As $C_4$-$C_{22}$ acyloxyalkylene, $R_5$ is for example 2-ethyl-2-acetoxymethyl-propylene.

The following compounds are examples of polyalkylpiperidine starting materials useful in making the hydroxylamine derivatives of formula C.

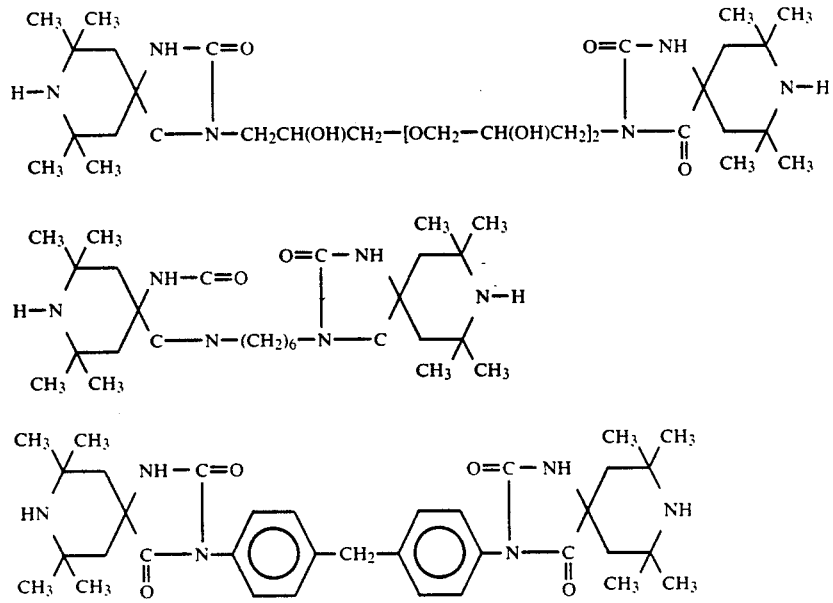

9-aza-8,8,10,10-tetramethyl-1,5-dioxaspiro[5.5]undecane,
9-aza-8,8,10,10-tetramethyl-3-ethyl-1,5-dioxaspiro[5.5]undecane,
2,2,6,6-tetramethylpiperidine-4-spiro-2'-(1',3'-dioxane)5'-spiro-5"-(1",3"-dioxane)-2"-spiro-4'''-(2''',2'''-6''',6'''-tetramethylpiperidine).

If any substituents are $C_2-C_6$ alkoxyalkyl, they are for example methoxymethyl, ethoxymethyl, propoxymethyl, tert-butoxyethyl, ethoxyethyl, ethoxypropyl, n-butoxyethyl, tert-butoxyethyl, isopropoxyethyl or propoxypropyl.

If $R_7$ is $C_3-C_5$ alkenyl, it is for example 1-propenyl, allyl, methallyl, 2-butenyl or 2-pentenyl.

As $C_7-C_9$ aralkyl, $R_7$ is in particular phenethyl or above all benzyl; and as $C_5-C_7$ cycloalkyl, $R_7$ is especially cyclohexyl.

If $R_7$ is $C_2-C_4$ hydroxyalkyl, it is for example 2-hydroxyethyl, 2-hydroxypropyl, 3-hydroxypropyl, 2-hydroxybutyl or 4-hydroxybutyl.

As $C_6-C_{10}$ aryl, the substituents are in particular phenyl, or alpha- or β-naphthyl which is unsubstituted, or substituted by halogen or $C_1-C_4$ alkyl.

If $R_7$ is $C_2-C_{12}$ alkylene, it is for example ethylene, propylene, 2,2-dimethylpropylene, tetramethylene, hexamethylene, octamethylene, decamethylene or dodecamethylene.

If $R_7$ is $C_6-C_{12}$ arylene, it is for example o-, m- or p-phenylene, 1,4-naphthylene or 4,4'-diphenylene.

If $Z'$ is $C_2-C_{12}$ alkanoyl, it is for example propionyl, butyryl, octanoyl, dodecanoyl or preferably acetyl.

The following compounds are examples of polyalkylpiperidine starting materials useful in making hydroxylamine derivatives of formula D.
3-benzyl-1,3,8-triaza-7,7,9,9-tetramethylspiro[4.5]decane-2,4-dione,
3-n-octyl-1,3,8-triaza-7,7,9,9-tetramethylspiro[4.5]decane-2,4-dione,
3-allyl-1,3,8-triaza-1,7,7,9,9-pentamethylspiro[4.5]decane-2,4-dione, or the compounds of the following formulae:

As $C_5-C_7$ cycloalkyl, $R_8$ is in particular cyclohexyl.

As $C_6-C_{10}$ aryl, $R_8$ is particularly phenyl, or alpha- or β-naphthyl which is unsubstituted or substituted with halogen or $C_1-C_4$ alkyl.

As $C_1-C_3$ alkylene, E is for example methylene, ethylene or propylene.

As $C_2-C_6$ alkylene, G is for example ethylene, propylene, 2,2-dimethylpropylene, tetramethylene or hexamethylene; and as $C_6-C_{12}$ arylene, G is o-, m- or p-phenylene, 1,4-naphthylene or 4,4'-diphenylene.

The following compounds are examples of polyalkylpiperidine starting materials useful in making the hydroxylamine derivatives of formula E.
N-hydroxymethyl-N'-2,2,6,6-tetramethylpiperidin-4-yl urea,
N-methoxymethyl-N'-2,2,6,6-tetramethylpiperidin-4-yl urea,
N-methoxymethyl-N'-n-dodecyl-N'-2,2,6,6-tetramethylpiperidin-4-yl-urea, and
O-(2,2,6,6-tetramethylpiperidin-4-yl)-N-methoxymethylurethane.

When the instant hydroxylamine derivative is of formula F, the following polymeric compounds are examples of starting materials useful in preparing said derivatives.

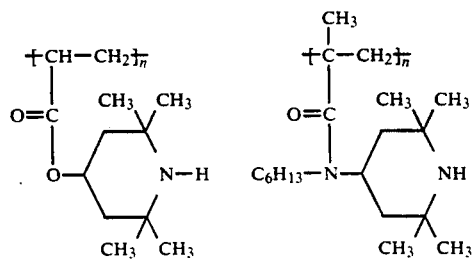

Additional starting hindered amine derivatives include for formula J:

poly-{[6-[(1,1,3,3-tetramethylbutyl)-imino]-1,3,5-triazine-2,4-diyl][2-(1-oxyl-2,2,6,6-tetramethylpiperidyl)-imino]-hexamethylene-4[4-(1-oxyl-2,2,6,6-tetramethylpiperidyl]-imino}, For compounds of formula O, $R_3$ is preferably $C_1$-$C_{12}$ alkyl and $C_5$-$C_7$ cycloalkyl and more preferably methyl, octyl, dodecyl and cyclohexyl.

For compounds of formula P, the following species are typical of tetracarboxylic acid dianhydrides suitable for the preparation thereof:

2,3,9,10-perylene tetracarboxylic acid dianhydride
1,4,5,8-naphthalene tetracarboxylic acid dianhydride
2,6-dichloronaphthalene-1,4,5,8-tetracarboxylic acid dianhydride
2,7-dichloronaphthalene-1,4,5,8-tetracarboxylic acid dianhydride
2,3,6,7-tetrachloronaphthalene-1,4,5,8-tetracarboxylic acid dianhydride
phenanthrene-1,8,9,10-tetracarboxylic acid dianhydride
2,3,3',4'-benzophenonetetracarboxylic acid dianhydride pyromellitic dianhydride
3,3',4,4'-benzophenonetetracarboxylic acid dianhydride
2,2',3,3'-benzophenonetetracarboxylic acid dianhydride
3,3',4,4'-biphenyltetracarboxylic acid dianhydride
2,2',3,3'-biphenyltetracarboxylic acid dianhydride
4,4'-isopropylidenediphthalic anhydride
3,3'-isopropylidenediphthalic anhydride
4,4'-oxydiphthalic anhydride
4,4'-sulfonyldiphthalic anhydride
3,3'-oxydiphthalic anhydride
4,4'-methylenediphthalic anhydride
4,4'-thiodiphthalic anhydride
4,4'-ethylidenediphthalic anhydride
2,3,6,7-naphthalenetetracarboxylic acid dianhydride
1,2,4,5-naphthalenetetracarboxylic acid dianhydride
1,2,5,6-naphthalenetetracarboxylic acid dianhydride
benzene-1,2,3,4-tetracarboxylic acid dianhydride
pyrazine-2,3,5,6-tetracarboxylic acid dianhydride.

The hydroxylamine derivatives of the instant invention are generally prepared by oxidizing the corresponding hindered amine with an appropriate peroxy compound such as hydrogen peroxide or tert-butyl hydroperoxide in the presence of a metal carbonyl or metal oxide catalyst followed by reduction of the oxyl intermediate formed to the desired N-hydroxy derivative, preferably by catalytic hydrogenation.

Thereafter, the N-acyloxy, N-carbamoyloxy and N-(alkoxyacyl)oxy derivatives are prepared by reacting the N-hydroxy hindered amine with the appropriate acid chloride, anhydride, cyanate, isocyanate or substituted chloroformate (for carbonates). The catalytic hydrogenation can also be conducted in acetic anhydride to prepare the N-acetoxy derivative.

The oxalates of formula N can be prepared by reacting (1-hydroxy-2,2,6,6-tetramethylpiperidin-4-yl)stearate, benzoate, and the like, with oxalyl chloride, or for $R_2$ being —NH—G'—NH by reacting the appropriate 1-hydroxy-2,2,6,6-tetramethyl piperidine with the appropriate diisocyanate.

These reactions are generally conducted at temperatures ranging from 0 to 60° C. and in a variety of solvents including toluene and dichloromethane. The reactions are also preferably conducted in the presence of an acid acceptor such as triethylamine. The various hindered amine precursors are largely commercially available or can be prepared by methods known in the art.

The derivatives are particularly effective in stabilizing organic materials against the degradative effects of actinic stimuli. Such organic materials include polyolefins, vinyl chloride polymers, elastomers, polyesters and polyurethanes. They are particularly active as light stabilizers in ambient cured and acid catalyzed thermoset coatings or enamels. Since these materials are considerably less basic than conventional hindered amines, they do not inhibit or interfere with cure as is encountered with the conventional hindered amines nor are they interacting. They likewise do not exhibit the color problems encountered with nitroxyl radicals and, unlike N-hydroxy hindered amines, tend to resist air oxidation during handling. Finally, the N-acyloxy hindered amines exhibit greater solubility in the solvents typically utilized in coatings. These areas are further described in U.S. application Ser. Nos. 07/099,411 and 07/099,420 both abandoned.

The following examples will further illustrate the embodiments of this invention.

EXAMPLE 1

Di-(1-acetoxy-2,2,6,6-tetramethylpiperidin-4-yl) Phthalate

A mixture of 20.0 g (42 mmol) of di-(1-oxyl-2,2,6,6-tetramethyl-piperidin-4-yl) phthalate, 100 ml of acetic anhydride, and 500 mg of 5% Pd on C is hydrogenated in a Paar apparatus (50 psi, ambient temperature, 1 hour). Catalyst is filtered and solvent is evaporated. The residue is dissolved in 150 ml of ethyl acetate. The ethyl acetate solution is washed with 5% aqueous ammonia (2 × 100 ml), water (100 ml), and saturated sodium chloride (100 ml), then dried over magnesium sulfate and concentrated to obtain a crude solid. The crude product is recrystallized from methanol to obtain 14.9 g (64% yield) of a white crystalline solid, m.p. 172–175° C.

| Anal. Calcd. for $C_{30}H_{44}N_2O_8$: | C, 64.3; | H, 7.9; | N, 5.0. |
|---|---|---|---|
| Found: | C, 64.5; | H, 8.2; | N, 5.1. |

EXAMPLE 2

Di-(1-acetoxy-2,2,6,6-tetramethylpiperidin-4-yl) Isophthalate

The compound is prepared according to the procedure given for Example 1 utilizing the isophthalate in place of the phthalate, m.p. 98–101° C.

| Anal. Calcd. for $C_{30}H_{44}N_2O_8$: | C, 64.3; | H, 7.9; | N, 5.0. |
|---|---|---|---|
| Found: | C, 62.4; | H, 8.0; | N, 5.0. |

EXAMPLE 3

Poly-{[6-[(1,1,3,3-tetramethylbutyl)-imino]-1,3,5-triazine-2,4-diyl] [2-(1-acetoxy-2,2,6,6-tetramethylpiperidyl)-imino]-hexamethylene-[4-(1-acetoxy-2,2,6,6-tetramethylpiperidyl)-imino]}

The compound is prepared according to the procedure given for Example 1, utilizing the corresponding 1-oxyl compound, m.p. 110–20° C. (glass transition)

| Anal. Calcd. for $(C_{39}H_{70}N_8O_4)_n$: | C, 65.5; | H, 9.9; | N, 15.7. |
|---|---|---|---|
| Found: | C, 65.6; | H, 9.4; | N, 13.0. |

EXAMPLE 4

Polymer of 1-acetoxy-4-acryloxy-2,2,6,6-tetramethylpiperidine

A solution of 20.0 g (74.3 mmol) of 1-acetoxy-4-acryloxy-2,2,6,6-tetramethylpiperidine and 0.19 g of azobisisobutyronitrile in 30 ml of dry toluene is added over 2 hr. to 25 ml of dry toluene maintained at 110° C. The reaction mixture is stirred an additional 15 minutes. A solution of 35 mg of n-dodecyl mercaptan in 2 ml of toluene is added, and the reaction mixture is then poured into cold hexane to yield a precipitate. The precipitate is dissolved in ether, and cold hexane is added to afford a white precipitate which is dried to give 16.4 g (82% yield) of a brittle glass. IR: 1755, 1720 cm$^{-1}$.

| Anal. Calcd. for $(C_{14}H_{23}NO_4)_n$: | C. 62.4; | H. 8.6; | N, 5.2. |
|---|---|---|---|
| Found: | C. 62.8; | H. 8.6; | N. 5.1. |

EXAMPLE 5

1-Acetoxy-2,2,6,6-tetramethylpiperidin-4-yl 4-Hydroxy-3,5-di-tert-butylbenzoate A solution of 20.0 g (92.9 mmol) of 1-acetoxy-4-hydroxy-2,2,6,6-tetramethylpiperidine in 10.3 g (102 mmol) of triethylamine and 210 ml of dichloromethane is cooled below 0° C. To this solution is added, under nitrogen, a solution of 25.0 g (92.9 mmol) of 4-hydroxy-3,5-di-tertbutylbenzoyl chloride over a 30 min. interval. During the addition the reaction temperature is maintained at −3 to 0° C. The reaction mixture is stirred at room temperature for 3 hours, then diluted with hexane (200 ml). Triethylamine hydrochloride is removed by filtration, and the filtrate is washed with 1N HCl (200 ml) and saturated sodium bicarbonate solution (200 ml). The solution is dried over magnesium sulfate and concentrated to an oil which is triturated in hexane to yield 1.5 g of a white solid impurity.

The mother liquor is concentrated and crystallized from methanol-dichloromethane to yield 11.6 g (28%) of a white solid, m.p. 154–56° C., which is the title compound.

| Anal. Calcd. for $C_{26}H_{41}NO_5$: | C. 69.7; | H. 9.2; | N. 3.1. |
|---|---|---|---|
| Found: | C. 69.7; | H. 9.4; | N. 3.1. |

EXAMPLE 6

Di-(1-acetoxy-2,2,6,6-tetramethylpiperidin-4-yl) 2-(4-Hydroxy-3,5-di-tert-butylbenzyl) n-butylmalonate To 10 mmol of lithium diisopropylamide in 25 ml of anhydrous tetrahydrofuran is added a solution of 27.6 g (50 mmol) of di-(1-acetoxy-2,2,6,6-tetramethylpiperidin-4-yl) n-butylmalonate in 90 ml of THF followed by a solution of 16.5 g (62.5 m mol) of 4-dimethylaminomethyl-2,6-di-tert-butylphenol in 50 ml THF. The reaction mixture is refluxed for 2 hours. The reaction mixture is concentrated under reduced pressure and the residue is dissolved in ether (300 ml). The ether solution is washed with 1N HCl (300 ml) and saturated sodium bicarbonate solution (150 ml), then dried over magnesium sulfate and concentrated. The resulting crude solid is recrystallized from hexane to give 25.7 g (66% yield) of a white solid. m.p. 174–175° C.

| Anal. Calcd. for $C_{44}H_{72}N_2O_9$: | C. 68.4; | H. 9.4; | N. 3.6. |
|---|---|---|---|
| Found: | C. 68.1; | H. 9.4; | N. 3.8. |

EXAMPLE 7

N-(1-Acetoxy-2,2,6,6-tetramethylpiperidin-4-yl)-N-(n-butyl)-4-(4-hydroxy-3,5-di-t-butylbenzoyloxy)-3,5-di-t-butylbenzamide A solution of 20.9 g (77.6 mmol) of 4-hydroxy-3,5-di-tert-butylbenzoyl chloride in 100 ml of dichloromethane is added dropwise over 30 min. under nitrogen to a chilled solution (0° C.) of 20.0 g (64.7 mol) of 1-acetoxy-4-butylamino-2,2,6,6-tetramethylpiperidine hydrochloride in 19.6 g (194 mmol) of triethylamine and 100 ml of dichloromethane. The reaction temperature is maintained below 5° C. during the addition. The reaction mixture is stirred for 3 hours at room temperature, then diluted with ether (200 ml) and filtered. The filtrate is washed with 1N HCl (2×100 ml) and sodium bicarbonate solution (200 ml). The solution is dried over magnesium sulfate, concentrated, and chromatographed on silica gel (3:1 hexane:ethyl acetate). The major reaction product is crystallized from methanol to yield 13.0 g of a white solid, m.p. 230–232° C.

| Anal. Calcd. for $C_{45}H_{70}N_2O_6$: | C. 73.5; | H. 9.6; | N. 3.8. |
|---|---|---|---|
| Found: | C. 72.6; | H. 9.4; | N. 3.7. |

EXAMPLE 8

N-(1-Acetoxy-2,2,6,6-tetramethylpiperidin-4-yl)-N-n-butyl-4-hydroxy-3,5-di-t-butylbenzamide A second recrystallization crop from Example 7 is recrystallized until a constant melting point is obtained. The yield is 4.4 g of a white solid. m.p. 161–64° C., with an analysis consistent with the title compound.

| Anal. Calcd. for $C_{30}H_{50}N_2O_4$: | C. 71.7; | H. 10.0; | N, 5.6. |
|---|---|---|---|
| Found: | C. 72.0; | H. 10.2; | N. 5.5. |

EXAMPLE 9

1,6-Di-[N-acetyl-N-(1-acetoxy-2,2,6,6-tetramethylpiperidin-4-yl)]-aminohexane A mixture of 52.8 g (310 mmol) of 1-oxyl-2,2,6,6-tetra methylpiperidin-4-one, 17.4 g (150 mmol) of 1,6-hexanediamine, methanol (10 0 ml), water (150 ml), and platinum oxide (500 mg) is hydrogenated in a Paar apparatus for 18 hours at 50 psi (ambient temperature). Chloroform (1000 ml) is added, and the catalyst is filtered. The organic phase is concentrated to obtain 44.4 g (69%) of 1,6-di-[N-(1-hydroxy-2,2,6,6-tetramethylpiperidin-4-yl)]-aminohexane. The hydroxylamine (19.5 g, 45.7 mmol) is added to 150 ml of acetic anhydride over 5 minutes, with the reaction temperature reaching 50° C. during the addition. The reaction mixture is refluxed for 30 minutes, then rehydrogenated (400 mg 5% Pd on C, 50 psi, 3 hr) to reduce any remaining nitroxyl radical. The catalyst is removed by filtration, and solvent is evaporated. The residue is crystallized from 4:1 toluene:heptane to give 14:1 g (52% yield) of a white solid, m.p. 169–70° C.

| Anal. Calcd. for $C_{32}H_{58}N_4O_6$: | C. 64.6; | H. 9.8; | N. 9.4. |
|---|---|---|---|
| Found: | C. 64.8; | H. 9.8. | N. 9.3. |

EXAMPLE 10

Di-(1-acetoxy-2,2,6,6-tetramethylpiperidin-4-yl) N,N'-(1,6-Hexanediyl)dicarbamate A mixture of 15.0 g (70 mmol) of 1-acetoxy-4-hydroxy-2,2,6,6-tetramethylpiperidine, 5.9 g (35 mmol) of 1,6-hexanediisocyanate, toluene (125 ml), and dibutyltin dilaurate (200 mg) is refluxed for 1 hour. The hot reaction mixture is poured into hexane (500 ml). The resulting precipitate is removed by filtration and triturated in ether to give 13.1 g (63% yield) of a white solid, m.p. 158–163° C.

| Anal. Calcd. for $C_{30}H_{54}N_4O_8$: | C. 60.2. | H. 9.1; | N. 9.4. |
|---|---|---|---|
| Found: | C. 60.1; | H. 9.1; | N. 10.0 |

EXAMPLE 11

1-Acetoxy-4-(N-acetyl-N-n-dodecylamino)-2,2,6,6-tetramethylpiperidine

A mixture of 42.6 g (250 mmol) of 1-oxyl-2,2,6,6-tetramethylpiperidin-4-one, 47.0 g (250 mmol) of n-dodecylamine, 600 mg of platinum oxide and 200 ml of toluene is hydrogenated in a Paar apparatus (50 psi, ambient temperature) for 3 hours. Acetic anhydride (77.9 g, 760 mmol) is added. The catalyst is removed by filtration, and the filtrate is refluxed for 3 hours. Solvent is evaporated at reduced pressure, and the residue is dissolved in 2:1 hexane:ether (500 ml). The solution is washed with 1N HCl (400 ml), saturated sodium bicarbonate solution (200 ml), and saturated sodium chloride solution (200 ml), then dried over magnesium sulfate and concentrated. The residue is chromatographed on silica gel (1:1 hexane:ethyl acetate) to obtain 42.4 g (40% yield) of a yellow oil.

| Anal. Calcd. for $C_{25}H_{48}N_2O_3$: | C. 70.7; | H. 11.4; | N. 6.6. |
|---|---|---|---|
| Found: | C. 71.0; | H. 11.3; | N. 6.3. |

EXAMPLE 12

Di-(4-n-octadecanoyloxy-2,2,6,6-tetramethylpiperidin-1-yl) Oxalate

A solution of 4.33g (34.1 mmol) of oxalyl chloride in 50 ml of dichloromethane is added dropwise over 20 minutes to a solution of 30.0 g (68.2 mmol) of 1-hydroxy-2,2,6,6-tetramethylpiperidin-4-yl) stearate in 8.3 g (81.8 mmol) of triethylamine and 100 ml of dichloromethane in a nitrogen atomosphere. The reaction temperature rises from 20° to 35° C. during the addition. The reaction mixture is stirred overnight at room temperature; the triethylamine hydrochloride formed is removed by filtration, and the filtrate is diluted to a total volume of 300 ml with dichloromethane. The solution is washed with 1N HCl (2 × 100 ml) and saturated sodium bicarbonate solution (200 ml), dried over magnesium sulfate, and concentrated to obtain a dark brown solid. The solid is suspended in methanol and filtered. The isolated solid is recrystallized twice from heptane (filtrol added to decolorize) to obtain 9.3g (29% yield) of white crystals. m.p. 104–5° C.

| Anal. Calcd. for $C_{56}H_{104}N_2O_8$: | C. 72.1; | H. 11.2; | N. 3.0. |
|---|---|---|---|
| Found: | C. 72.1; | H. 11.3; | N. 3.2. |

EXAMPLE 13

Di-(4-benzoyloxy-2,2,6,6-tetramethylpiperidin-1-yl) Oxalate

The compound is prepared according to the procedure given for Example 12, utilizing the corresponding benzoate, m.p. 244° C(dec).

| Anal. Calcd. for $C_{34}H_{44}N_2O_8$: | C. 67.1; | H. 7.3; | N. 4.6. |
|---|---|---|---|
| Found: | C. 66.8; | H. 7.4; | N. 4.5. |

EXAMPLE 14

Di-(1-benzoyloxy-2,2,6,6-tetramethylpiperidin-4-yl) Sebacate

Benzoyl chloride (29.5 g, 210 mmol) is added dropwise over 30 minutes to a mixture of 51.3g (100 mmol) of di-(1-hydroxy-2,2,6,6-tetramethylpiperidin-4-yl) sebacate, 250 ml of toluene, and 30.4 g (300 mmol) of triethylamine under nitrogen. The temperature rises from 22° to 48° C. during the addition. The reaction mixture is then heated at 70° C. for 45 minutes, cooled below 40° C., and diluted with 150 ml of toluene. Triethylamine hydrochloride is filtered off, and the filtrate is washed with 10% aqueous ammonia (200 ml), warm water (3×400 ml), 1N HCl (2×200 ml), saturated sodium bicarbonate solution (200 ml) and saturated sodium chloride solution (200 ml). The solution is dried over magnesium sulfate and concentrated. The residue is recrystallized from methanol to obtain 51.5 g (71% yield) of a white solid, m.p. 92–100° C.

| Anal. Calcd. for $C_{42}H_{60}N_2O_8$: | C. 70.0; | H. 8.4; | N. 3.9. |
|---|---|---|---|
| Found: | C. 69.8; | H. 8.6; | N. 3.9. |

EXAMPLE 15

1-Benzoyloxy-4-(N-n-butyl-N-benzoylamino)-2,2,6,6-tetramethylpiperidine

The compound is prepared from the reaction of 1-hydroxy-4-(N-n-butylamino)-2,2,6,6-tetramethylpiperidine with benzoyl chloride following a procedure similar to that used for Example 14, m.p. 155–59° C.

| Anal. Calcd. for $C_{27}H_{36}N_2O_3$: | C. 74.3; | H. 8.3; | N. 6.4. |
|---|---|---|---|
| Found: | C. 74.0. | H. 8.4. | N. 6.3. |

EXAMPLE 16

(1-Benzoyloxy-2,2,6,6-tetramethylpiperidin-4-yl)(1'-Benzyloxy-2,2,6,6-tetramethylpiperidin-4-yl)Isophthalate A mixture of 35.0 g (78.7 mmol) of di-(2,2,6,6-tetramethylpiperidin-4-yl) isophthalate, 1.0 g of molybdenum hexacarbonyl, and 75 ml of toluene is heated to 90° C. in a nitrogen atmosphere. A solution of 4.2M t-butyl hydroperoxide in toluene (225 ml, 945 mmol) is added over 5 minutes and the reaction mixture turns red. After the addition, the reaction mixture is irradiated for 6 hours (internal temperature 85° C.) with a UV lamp. Another 1.0g portion of molybdenum hexacarbonyl is added, and the reaction mixture is irradiated for 16 hours. The mixture was then filtered and concentrated and the crude residue is chromatographed on silica gel (9:1 hexane: ethyl acetate). The more polar of the two major reaction products is recrystallized from ethanol to obtain 12.0g (23% yield) of the title compound, a white solid with m.p. 137–40° C.

| Anal. Calcd. for $C_{40}H_{50}N_2O_7$: | C, 71.6; | H, 7.5; | N, 4.2. |
|---|---|---|---|
| Found: | C, 71.7; | H, 7.8; | N, 4.4. |

EXAMPLE 17

1,4-Di-(4-hydroxy-3-5,-di-tert-butylbenzoyloxy)-2,2,6,6-tetramethylpiperidine

A solution of 31.2 g (116 mmol) of 4-hydroxy-3,5-di-tert-butylbenzoyl chloride in 100 ml of toluene is added dropwise over 3 minutes to a mixture of 10.0 g (58.8 mmol) of 1,4-dihydroxy-2,2,6,6-tetramethylpiperidine and 15.5 g (128 mmol) of N,N-dimethylaniline in 50 ml of toluene in a nitrogen atmosphere. The reaction mixture is heated at 80° C. for three hours, then diluted to 400 ml. The solution is washed with 1N HCl, saturated sodium bicarbonate solution, and saturated sodium chloride solution, then dried over magnesium sulfate and concentrated. The yellow residue is decolorized with DARCO G-60 in 2-propanol. Crystallization gives 14.0 g (38% yield) of a white solid, m.p. 196° C.(dec).

| Anal. Calcd. for $C_{30}H_{50}NO_6$: | C, 73.4; | H, 9.3; | N, 2.2. |
|---|---|---|---|
| Found: | C, 73.3; | H, 9.3; | N, 2.1. |

EXAMPLE 18

1-Carbamoyloxy-4-benzoyloxy-2,2,6,6-tetramethylpiperidine

A solution of 6.7 ml of 12 N HCl in 10 ml of water is added dropwise over 10 minutes with cooling below 0° C. to a suspension of 20.8 g (75 mmol) of 1-hydroxy-4-benzoyloxy-2,2,6,6-tetramethylpiperidine, 75 ml of methanol, and 25 ml of water in a nitrogen atmosphere. A clear solution resulted. A solution of 6.1 g (75 mmol) of potassium cyanate in 25 ml of water is added dropwise over 30 minutes. The reaction temperature is maintained at 0–5° C. during the cyanate addition. The reaction mixture is stirred 30 minutes at ambient temperature, then filtered. The precipitate is washed with water, then dissolved in 200 ml of toluene. Residual water is removed by azeotropic distillation. The toluene solution is then cooled to yield 19.4 g (81%) of a white crystalline solid, m.p. 148–49° C.

| Anal. Calcd. for $C_{17}H_{24}N_2O_4$: | C, 63.7; | H, 7.6; | N, 8.7. |
|---|---|---|---|
| Found: | C, 63.5; | H, 7.8; | N, 8.8. |

EXAMPLE 19

Di-(1-carbamoyloxy-2,2,6,6-tetramethylpiperidin-4-yl) Sebacate

The compound is prepared according to the procedure given in Example 18.

| Anal. Calcd. for $C_{30}H_{54}N_4O_8$: | C, 60.2; | H, 9.1; | N, 9.4. |
|---|---|---|---|
| Found: | C, 60.3; | H, 9.0; | N, 9.1. |

EXAMPLE 20

Di-(1-phenylcarbamoyloxy-2,2,6,6-tetramethylpiperidin-4-yl) Sebacate

Phenyl isocyanate (9.5 g, 80 mmol) is added over 5 minutes to a suspension of 20.0 g (39 mmol) of di-(1-hydroxy-2,2,6,6-tetramethylpiperidin-4-yl) sebacate in 125 ml of dichloromethane. The resulting solution is refluxed for 30 minutes and then evaporated to obtain a solid. The crude solid is briefly refluxed in methanol, filtered off, and recrystallized from 2-propanol: dichloromethane to give 22.2g (76% yield) of white solid, m.p. 159–61° C.(dec).

| Anal. Calcd. for $C_{42}H_{62}N_4O_8$: | C, 67.2; | H, 8.3; | N, 7.5. |
|---|---|---|---|
| Found: | C, 66.9; | H, 8.3. | N, 7.3. |

EXAMPLE 21

4-Benzoyloxy-1-n-butylcarbamoyloxy-2,2,6,6-tetramethylpiperidine

A solution of 4.66 g (40 mmol) of n-butyl isocyanate in 10 ml of toluene is added over 10 minutes to a suspension of 10.6 g (38.2 mmol) of 1-hydroxy-4-benzoyloxy-2,2,6,6-tetramethylpiperidine in 40 ml of toluene. The reaction mixture is heated at 50° C. for 30 minutes. The reaction mixture is then filtered, and the residue from evaporation of the filtrate is crystallized from hexane to give 4.2 g (29% yield) of a white solid, m.p. 126–27° C.

| Anal. Calcd. for $C_{21}H_{32}N_2O_4$: | C, 67.0; | H, 8.6; | N, 7.5. |
|---|---|---|---|
| Found: | C, 67.2; | H, 8.7; | N, 7.4. |

EXAMPLE 22

Di-(1-n-butylcarbamoyloxy-2,2,6,6-tetramethylpiperidin-4-yl) Phthalate

The compound is prepared in 65% yield according to the procedure given in Example 21, except that the appropriate phthalate and dichloromethane solvent are utilized, m.p. 180–82° C.

| Anal. Calcd. for $C_{36}H_{58}N_4O_8$: | C, 64.1; | H, 8.7; | N, 8.3. |
|---|---|---|---|
| Found: | C, 63.9. | H, 8.8. | N, 8.0. |

EXAMPLE 23

Di-(1-n-butylcarbamoyloxy-2,2,6,6-tetramethylpiperidin-4-yl) Isophthalate

The compound is prepared according to the procedure given in Example 22 except for the use of the isophthalate, m.p. 176–77° C.

| | | | |
|---|---|---|---|
| Anal. Calcd. for $C_{36}H_{58}N_4O_8$: | C, 64.1; | H, 8.7; | N, 8.3. |
| Found: | C, 64.1. | H, 8.4. | N, 8.3. |

EXAMPLE 24

Di-(1-n-butylcarbamoyloxy-2,2,6,6-tetramethylpiperidin-4-yl) 2,2-Diethylmalonate The compound is prepared according to the procedure given in Example 22 except for the use of the appropriate malonate, m.p. 166–69° C.

| | | | |
|---|---|---|---|
| Anal. Calcd. for $C_{35}H_{64}N_4O_8$: | C, 62.8; | H, 9.6; | N, 8.4. |
| Found: | C, 63.2; | H, 9.6; | N, 8.3. |

EXAMPLE 25

Di-(1-n-butylcarbamoyloxy-2,2,6,6-tetramethylpiperidin-4-yl) n-Butylmalonate

The compound is prepared according to the procedure given in Example 22. m.p. 129–131° C.

| | | | |
|---|---|---|---|
| Anal. Calcd. for $C_{35}H_{64}N_4O_8$: | C, 62.8; | H, 9.6; | N, 8.4. |
| Found: | C, 63.1; | H, 9.5; | N, 8.3. |

EXAMPLE 26

Di-(4-benzoyloxy-2,2,6,6-tetramethylpiperdin-1-yl) N,N'-(2,4,4-trimethyl-1,6-hexanediyl)-dicarbamate The compound is prepared from 4-benzoyloxy-1-hydroxy-2,2,6,6-tetramethylpiperidine and 2,4,4-trimethylhexane-1,6-diisocyanate according to the procedure given in Example 21, m.p. 165–67° C.

| | | | |
|---|---|---|---|
| Anal. Calcd. for $C_{43}H_{64}N_4O_8$: | C, 67.5; | H, 8.4; | N, 7.3. |
| Found: | C, 67.4; | H, 9.0; | N, 7.4. |

EXAMPLE 27 n-Butyl-(1-benzoyloxy-2,2,6,6-tetramethylpiperidin-4-yl) Carbonate

A solution of 7.8 g (81 mmol) of n-butylchloroformate in 15 ml of toluene is added dropwise over 20 minutes to a mixture of 15.0 g (54 mmol) of 1-hydroxy-4-benzoyloxy-2,2,6,6-tetramethylpiperidine, 8.2 ml (101 mmol) of triethylamine, and 75 ml of toluene in a nitrogen atmosphere. During the addition, the reaction temperature is maintained below 10° C. with an ice bath. After the addition is complete, the reaction mixture is stirred two hours at room temperature. Triethylamine hydrochloride is filtered, the filtrate washed with 1N HCl (200 ml), saturated sodium bicarbonate (200 ml), and saturated sodium chloride (200 ml), then dried over magnesium sulfate and concentrated. The resulting oil is crystallized from hexane to give 14.1 g (69% yield) of a white solid, m.p. 83–84° C.

| | | | |
|---|---|---|---|
| Anal. Calcd. for $C_{21}H_{31}NO_4$: | C, 66.8. | H, 8.3; | N, 3.7. |
| Found: | C, 66.8; | H, 8.4; | N, 3.9. |

Summarizing, this invention is seen to provide a series of new O-acyl, O-carbamoyl and O-carbonate substituted N-hydroxy hindered amine stabilizers. Variations may be made in proportions, procedures and materials without departing from the scope of the invention as defined by the following claims.

What is claimed is:

1. A compound corresponding to the formulae (A)

(B)

(C)

(D)

(E)

(F)

-continued

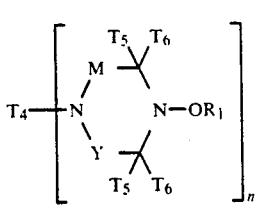
(G)

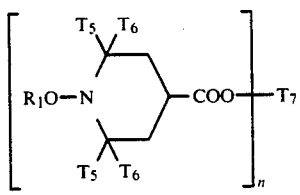
(H)

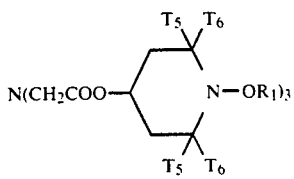
(I)

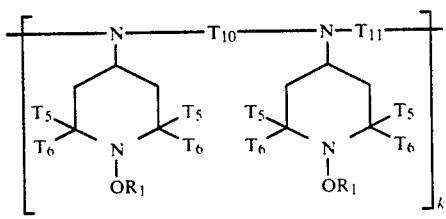
(J)

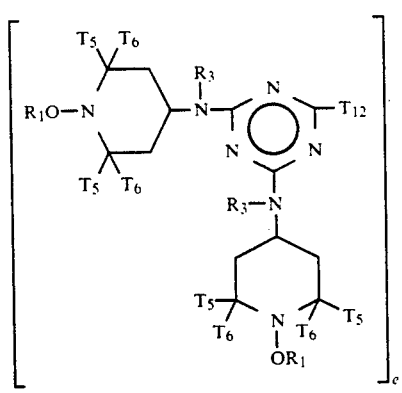
(K)

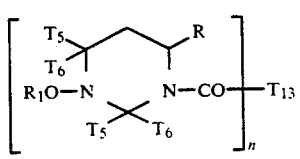
(L)

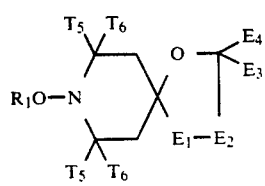
(M)

-continued

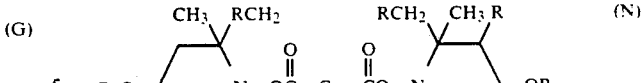
(N)

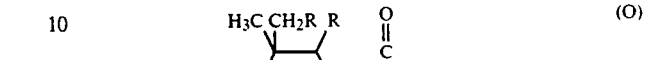
(O)

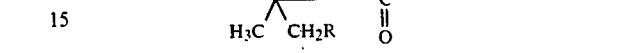
(P)

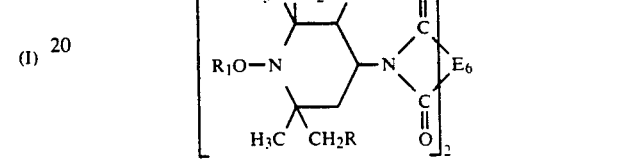

wherein
R is hydrogen or methyl,
$R_1$ is

wherein D is $C_1$-$C_{18}$ alkyl, $C_1$-$C_{18}$ alkoxy, phenyl, phenyl substituted by hydroxy, alkyl or alkoxy, or amino or amino mono- or disubstituted by alkyl or phenyl;
m is 1-4,
when m is 1,
$R_2$ is

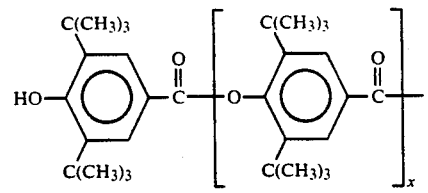

wherein x is 0 or 1, or

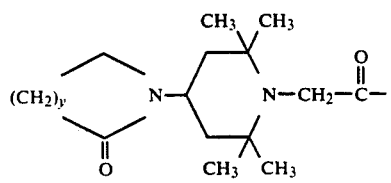

wherein y is 2-4;
when m is 2 and D is alkyl, phenyl or substituted phenyl,
$R_2$ is $C_1$-$C_{12}$ alkylene, $C_4$-$C_{12}$ alkenylene, xylylene, a divalent acyl radical or a cycloaliphatic, araliphatic or aromatic dicarboxylic acid or of a dicarbamic acid,

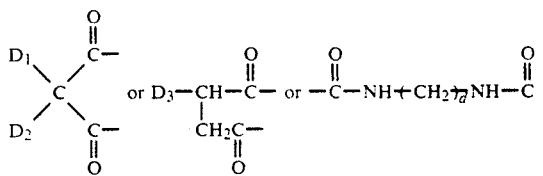

wherein $D_1$ is an aryl, aralkyl or 3,5-di-t-butyl-4-hydroxybenzyl radical, $D_2$ is $D_1$ or hydrogen, $D_3$ is an alkenyl radical containing up to 18 carbon atoms, and d is 0–20;

when m is 2 and D is amino, substituted amino or alkoxy, $R_2$ is $C_1$–$C_{12}$ alkenylene, xylylene, a divalent acyl radical of an aliphatic, cycloaliphatic, araliphatic or aromatic dicarboxylic acid or of a dicarbamic acid;

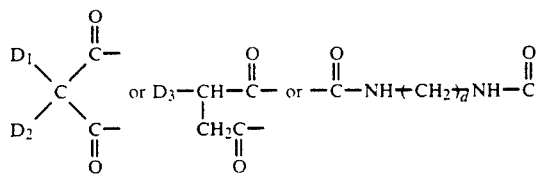

wherein $D_4$ and $D_5$ are independently hydrogen, an alkyl radical containing up to 8 carbon atoms, an aryl, aralkyl or 3,5-di-t-butyl-4-hydroxybenzyl radical, $D_6$ is hydrogen, or an alkyl or alkenyl radical containing up to 18 carbon atoms, and d is 0–20;

when m is 3, $R_2$ is a trivalent acyl radical of an aliphatic, unsaturated aliphatic, cycloaliphatic, or aromatic tricarboxylic acid;

when m is 4, $R_2$ is a tetravalent acyl radical of a saturated or unsaturated aliphatic or aromatic tetracarboxylic acid;

p is 1, 2 or 3, $R_3$ is hydrogen, $C_1$–$C_{12}$ alkyl, $C_5$–$C_7$ cycloalkyl, $C_7$–$C_9$ aralkyl, $C_2$–$C_{18}$ alkanoyl, $C_3$–$C_5$ alkenoyl or benzoyl;

when p is 1, $R_4$ is hydrogen, $C_1$–$C_{18}$ alkyl, $C_5$–$C_7$ cycloalkyl, $C_2$–$C_8$ alkenyl unsubstituted or substituted by a cyano, carbonyl or carbamide group, aryl, aralkyl, or it is glycidyl, a group of the formula —CH$_2$—CH(OH)—Z or of the formula —CO—Z— or —CONH—Z wherein Z is hydrogen, methyl or phenyl; or a group of the formulae

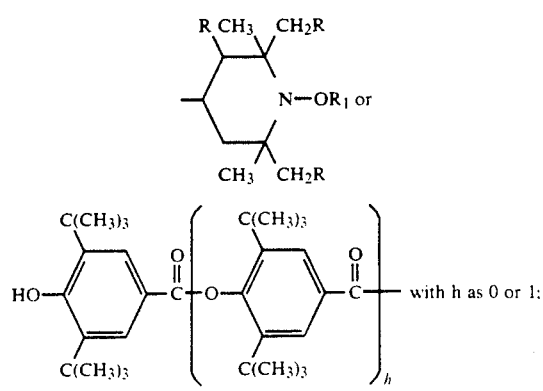

or $R_3$ and $R_4$ together with p is 1 can be alkylene of 4 to 6 carbon atoms or 2-oxopolyalkylene or the cyclic acyl radical of an aliphatic or aromatic 1,2- or 1,3-dicarboxylic acid, when p is 2, $R_4$ is a direct bond or is $C_1$–$C_{12}$ alkylene, $C_6$–$C_{12}$ arylene, xylylene, a —CH$_2$CH(OH)—CH$_2$ group, or a group —CH$_2$—CH(OH)—CH$_2$—O—X—X—O—CH$_2$—CH(OH)—CH$_2$— wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—; or $R_4$ is

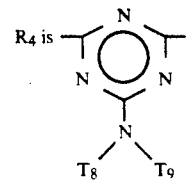

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, when p is 3, $R_4$ is 2,4,6-triazinyl, when n is 1, $R_5$ and $R'_5$ are independently $C_1$–$C_{12}$ alkyl, $C_2$–$C_{12}$ alkenyl, $C_7$–$C_{12}$ aralkyl, or $R_5$ is also hydrogen, or $R_5$ and $R'_5$ together are $C_2$–$C_8$ alkylene or hydroxyalkylene or $C_4$–$C_{22}$ acyloxyalkylene;

when n is 2, $R_5$ and $R'_5$ together are (—CH$_2$)$_2$C(CH$_2$—)$_2$;

$R_6$ is hydrogen, $C_1$–$C_{12}$ alkyl, allyl, benzyl, glycidyl or $C_2$–$C_6$ alkoxyalkyl;

when n is 1, $R_7$ is hydrogen, $C_1$–$C_{12}$ alkyl, $C_3$–$C_5$ alkenyl, $C_7$–$C_9$ aralkyl, $C_5$–$C_7$ cycloalkyl, $C_2$–$C_4$ hydroxyalkyl, $C_2$–$C_6$ alkoxyalkyl, $C_6$–$C_{10}$ aryl, glycidyl, a group of the formula —(CH$_2$)$_m$—COO—Q or of the formula —(CH$_2$)$_m$—O—CO—Q wherein m is 1 or 2, and Q is $C_1$–$C_4$ alkyl or phenyl; or when n is 2, $R_7$ is $C_2$–$C_{12}$ alkylene, $C_6$–$C_{12}$ arylene, a group —CH$_2$CH(OH)—CH$_2$—O—X—O—CH$_2$—CH(OH)—CH$_2$— wherein X is $C_2$–$C_{10}$ alkylene, $C_6$–$C_{15}$ arylene or $C_6$–$C_{12}$ cycloalkylene, or a group —CH$_2$CH(OZ')CH$_2$—(OCH$_2$—CH(OZ')CH$_2$)$_2$— wherein Z' is hydrogen, $C_1$–$C_{18}$ alkyl, allyl, benzyl, $C_2$–$C_{12}$ alkanoyl or benzoyl;

$Q_1$ is —N($R_8$)— or —O—; E is $C_1$–$C_3$ alkylene, he group —CH$_2$—CH($R_9$)—O— wherein $R_9$ is hydrogen, methyl or phenyl the group —(CH$_2$)$_3$—NH— or a direct bond;

$R_{10}$ is hydrogen or $C_1$–$C_{18}$ alkyl;

$R_8$ is hydrogen, $C_1$–$C_{18}$ alkyl, $C_5$–$C_7$ cycloalkyl, $C_7$–$C_{12}$ aralkyl, cyanoethyl, $C_6$–$C_{10}$ aryl, the group —CH$_2$—CH($R_9$)—OH wherein $R_9$ has the meaning defined above; a group of the formula

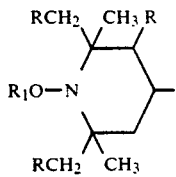

or a group of the formula

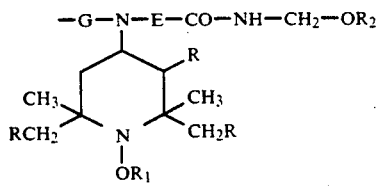

wherein G can be $C_2$-$C_6$ alkylene or $C_6$-$C_{12}$ arylene; or $R_8$ is a group $-E-CO-NH-CH_2-OR_{10}$;

$T_3$ is ethylene or 1,2-propylene, or is the repeating structural unit derived from an alpha-olefin copolymer with an alkyl acrylate or methacrylate; k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene, M and Y are independently methylene or carbonyl;

$T_7$ is the same as $R_7$.

$T_{10}$ and $T_{11}$ are independently alkylene of 2 to 12 carbon atoms, or $T_{11}$ is

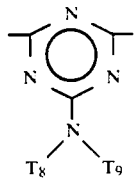

$T_{12}$ is piperazinyl,

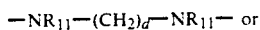

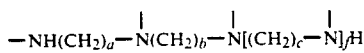

where $R_{11}$ is the same as $R_3$ or is also

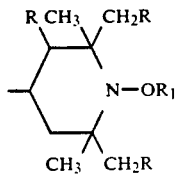

a, b and c are independently 2 or 3, and f is 0 or 1, e is 3 or 4, $T_{13}$ is the same as $R_4$ with the proviso that $T_{13}$ cannot be hydrogen when p is 1;

$E_1$ and $E_2$, being different, each are $-CO-$ or $N(E_5)-$ wherein $E_5$ is hydrogen, $C_1$-$C_{12}$ alkyl or $C_4$-$C_{22}$ alkoxycarbonylalkyl;

$E_3$ is hydrogen, alkyl of 1 to 30 carbon atoms, phenyl, naphthyl, said phenyl or said napthyl substituted by chlorine or by alkyl of 1 to 4 carbon atoms, or phenylalkyl of 7 to 12 carbon atoms, or said phenylalkyl substituted by alkyl of 1 to 4 carbon atoms;

$E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms;

$R_2$ of formula (N) is as previously defined when m is 1;

$G_2$ is a direct bond, $C_1$-$C_{12}$ alkylene, phenylene or $-NH-G'-NH$ wherein $G'$ is $C_1$-$C_{12}$ alkylene; and $E_6$ is an aliphatic or aromatic tetravalent radical.

2. A compound of claim 1, wherein D is $C_1$-$C_{18}$ alkyl, phenyl or phenyl substituted by hydroxy, alkyl or alkoxy.

3. The compound of claim 2 selected from the group consisting of
di-(1-acetoxy-2,2,6,6-tetramethylpiperidin-4-yl) phthalate,
di-(1-acetoxy-2,2,6,6-tetramethylpiperidin-4-yl) isophthalate,
poly-{[6-[(1,1,3,3-tetramethylbutyl)-imino]-1,3,5-triazine-2,4-diyl][2-(1-acetoxy-2,2,6,6-tetramethylpiperidyl)imino]-hexamethylene-[4-(1-acetoxy-2,2,6,6-tetramethylpiperidyl)-imino]},
polymer of 1-acetoxy-4-acryloxy-2,2,6,6-tetramethylpiperidine,
1-acetoxy-2,2,6,6-tetramethylpiperidin-4-yl 4-hydroxy-3,5-di-tert-butylbenzoate,
di-(1-acetoxy-2,2,6,6-tetramethylpiperidin-4-yl) 2-(4-hydroxy-3,5-di-tert-butylbenzyl) n-butylmalonate,
N-(1-acetoxy-2,2,6,6-tetramethylpiperidin-4-yl)-N-(n-butyl)-4-(4-hydroxy-3,5-di-t-butylbenzoyloxy)-3,5-di-t-butylbenzamide,
N-(1-acetoxy-2,2,6,6-tetramethylpiperidin-4-yl)-N-n-butyl-4-hydroxy-3,5-di-t-butylbenzamide,
1,6-di-[N-acetyl-N-(1-acetoxy-2,2,6,6-tetramethylpiperidin-4yl)]-aminohexane,
di-(1-acetoxy-2,2,6,6-tetramethylpiperidin-4-yl) N,N'-(1,6-hexanediyl)diacarbamate,
1-acetoxy-4-(N-acetyl-N-n-dodecylamino)-2,2,6,6-tetramethyl piperidine,
di-(1-benzoyloxy-2,2,6,6-tetramethylpiperidin-4-yl sebacate,
1-benzoyloxy-4-(N-n-butyl-N-benzoylamino)-2,2,6,6-tetramethylpiperidine,
(1-benzoyloxy-2,2,6,6-tetramethylpiperidin-4-yl) 1'-benzyloxy-2,2,6,6-tetramethylpiperidin-4-yl)isophthalate, and
1,4-di-(4-hydroxy-3-5,-di-tert-butylbenzoyloxy)-2,2,6,6-tetramethylpiperidine 4. A compound of claim 1, wherein D is amino or amino mono- or di-substituted by alkyl or phenyl.

5. The compound of claim 4 selected from the group consisting of
1-carbamoyloxy-4-benzoyloxy-2,2,6,6-tetramethylpiperidine,
di-(1-carbamoyloxy-2,2,6,6-tetramethylpiperidin-4-yl) sebacate,
di-(1-phenylcarbamoyloxy-2,2,6,6-tetramethylpiperidin-4-yl) sebacate,
4-benzoyloxy-1-n-butylcarbamoyloxy-2,2,6,6-tetramethylpiperidine.

di-(1-n-butylcarbamoyloxy-2,2,6,6-tetramethylpiperidin-4-yl) phthalate, di-(1-n-butylcarbamoyloxy-2,2,6,6-tetramethylpiperidin-4-yl isophthalate, di-(1-n-butylcarbamoyloxy-2,2,6,6-tetramethylpiperidin-4-yl 2,2-diethylmalonate, and di-(1-n-butylcarbamoyloxy-2,2,6,6-tetramethylpiperidin-4-yl n-butylmalonate.

6. A compound of claim 1, wherein D is $C_1$–$C_{18}$ alkoxy.

7. n-Butyl-(1-benzoyloxy-2,2,6,6-tetramethylpiperidin-4-yl) carbonate according to claim 6.

8. A compound of formulae (A), (B), (H)–(K), (M) or (N) according to claim 1.

9. The compound of the formula (N) according to claim 8 selected from the group consisting of
di-(4-n-octadecanoyloxy-2,2,6,6-tetramethylpiperidin-1-yl) oxalate,
di-(4-benzoyloxy-2,2,6,6-tetramethylpiperidin-1-yl oxalate, and
di-(4-benzyloxy-2,2,6,6-tetramethylpiperdin-1-yl) N,N'-(2,4,4-trimethyl-1,6hexanediyl)-dicarbamate.

* * * * *